(12) United States Patent
Belliappa

(10) Patent No.: US 10,285,862 B2
(45) Date of Patent: May 14, 2019

(54) SLEEP MASK APPARATUS

(71) Applicant: RADICLES, INC., New York, NY (US)

(72) Inventor: Ajit Belliappa, New York, NY (US)

(73) Assignee: RADICLES, INC., New York, NY (US)

( * ) Notice: Subject to any disclaimer, the term of this patent is extended or adjusted under 35 U.S.C. 154(b) by 93 days.

(21) Appl. No.: 14/657,729

(22) Filed: Mar. 13, 2015

(65) Prior Publication Data
US 2016/0262936 A1    Sep. 15, 2016

(51) Int. Cl.
A61F 9/04    (2006.01)

(52) U.S. Cl.
CPC ...................................... *A61F 9/04* (2013.01)

(58) Field of Classification Search
CPC .... A61F 13/1169; A61F 13/1184; A61F 9/04; A61F 13/124; A61F 9/045; A61F 2013/00497; A61F 13/12
USPC .............................. 2/15, 11, 173, 12; 128/858
See application file for complete search history.

(56) References Cited

U.S. PATENT DOCUMENTS

| | | | |
|---|---|---|---|
| 1,886,725 A * | 11/1932 | Pedersen | A61F 9/04 2/15 |
| 2,874,385 A | 2/1959 | Wade | |
| 3,068,863 A | 12/1962 | Bowman | |
| 3,092,103 A | 6/1963 | Mower | |
| 4,019,516 A * | 4/1977 | D'Auria | A61F 9/04 604/308 |
| 4,122,847 A * | 10/1978 | Craig | A61F 9/026 128/858 |
| 4,331,136 A * | 5/1982 | Russell | A61F 9/04 128/858 |

(Continued)

FOREIGN PATENT DOCUMENTS

| | | |
|---|---|---|
| CN | 2107904 U | 6/1992 |
| CN | 2200426 Y | 6/1995 |

(Continued)

OTHER PUBLICATIONS

Authorized Officer Thomas, Shane, "The International Search Report and the Written Opinion of the International Searthing Authority, or the Declaration" dated Jun. 3, 2016. PCT/US2016/021237. 11 Pages.

*Primary Examiner* — Anna K Kinsaul
*Assistant Examiner* — F Griffin Hall
(74) *Attorney, Agent, or Firm* — Stetina Brunda Garred and Brucker

(57) ABSTRACT

A sleep mask apparatus for use over a user's eyes. The sleep mask apparatus includes an opaque element having an inner surface and an opposing outer surface. The opaque element is sized and configured to extend across both of the user's eyes to mitigate the passage of light toward the user's eyes with the inner surface facing the user and the outer surface facing away from the user. A support element is coupled to the opaque element and includes a first support surface and an opposing second support surface. The inner surface of the opaque element is offset from the first support surface. The support element defines a peripheral margin extending around the opaque element, with the first support surface having an adhesive applied thereto at the peripheral margin to facilitate adhering of the support element to the user.

22 Claims, 6 Drawing Sheets

(56) References Cited

U.S. PATENT DOCUMENTS

| | | | | |
|---|---|---|---|---|
| 4,635,625 A * | 1/1987 | Teeple | ............... | A61F 9/04 128/858 |
| 4,649,908 A * | 3/1987 | Ghaly | ............... | A61F 9/04 128/858 |
| 4,727,869 A | 3/1988 | Leonardi | | |
| 4,862,902 A * | 9/1989 | Goffman | ............... | A61F 9/04 128/858 |
| 4,872,217 A * | 10/1989 | Kitayama | ............... | A61F 9/04 2/15 |
| 4,951,658 A | 8/1990 | Morgan et al. | | |
| 5,435,006 A * | 7/1995 | Kitayama | ............... | A61F 9/04 2/15 |
| 5,613,502 A | 3/1997 | Lee | | |
| 5,769,806 A | 6/1998 | Radow | | |
| 5,879,292 A | 3/1999 | Sternberg et al. | | |
| 5,918,600 A | 7/1999 | Durette | | |
| 5,940,886 A * | 8/1999 | McCarthy Smith | ... | A61F 11/12 2/15 |
| 6,543,056 B2 * | 4/2003 | Spiteri | ............... | A61F 9/04 2/15 |
| 7,036,928 B2 | 5/2006 | Schwebel | | |
| 7,231,922 B2 * | 6/2007 | Davison | ............... | A61F 9/029 128/858 |
| 7,748,387 B1 * | 7/2010 | Vu | ............... | A61F 9/04 128/858 |
| 8,458,812 B2 | 6/2013 | Kayerod | | |
| 8,966,662 B2 * | 3/2015 | Belliappa | ............... | A61F 9/04 2/15 |
| 9,144,518 B2 * | 9/2015 | Belliappa | ............... | A61F 9/04 |
| 2003/0056281 A1 * | 3/2003 | Hasegawa | ............... | A61F 7/02 2/428 |
| 2005/0229281 A1 * | 10/2005 | Glasser | ............... | A61F 9/04 2/15 |
| 2009/0255026 A1 * | 10/2009 | Benner | ............... | A61F 9/04 2/12 |
| 2009/0260633 A1 * | 10/2009 | Vreman | ............... | A61F 9/04 128/858 |
| 2010/0122398 A1 * | 5/2010 | Luciano | ............... | A61F 9/04 2/173 |
| 2012/0192330 A1 | 8/2012 | McMullen | | |
| 2014/0182039 A1 * | 7/2014 | Belliappa | ............... | A61F 9/045 2/15 |
| 2015/0164693 A1 * | 6/2015 | Belliappa | ............... | A61F 9/04 2/15 |

FOREIGN PATENT DOCUMENTS

| | | |
|---|---|---|
| CN | 201157456 Y | 12/2008 |
| CN | 201676078 U | 12/2010 |
| EP | 0732108 | 9/1996 |
| JP | 3142860 U | 6/2008 |
| KR | 200427260 Y1 | 9/2006 |
| RU | 41984 U1 | 11/2004 |

\* cited by examiner

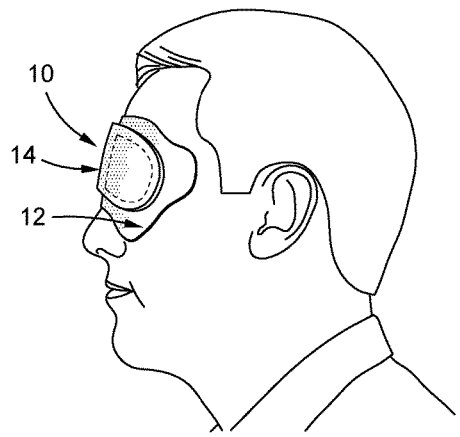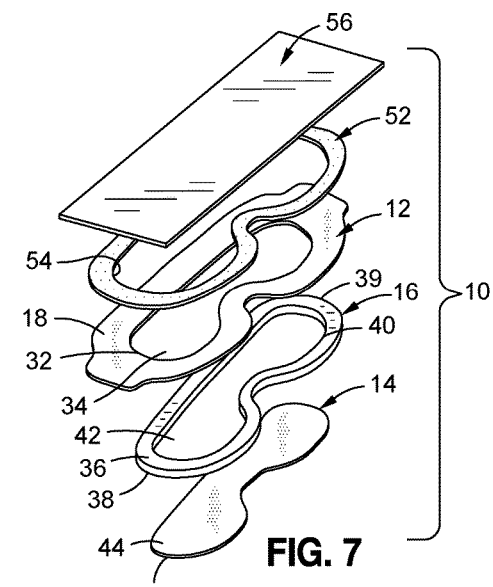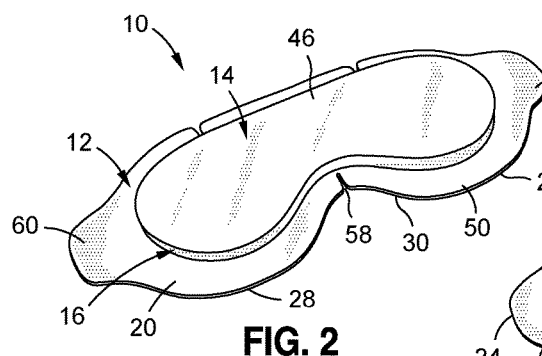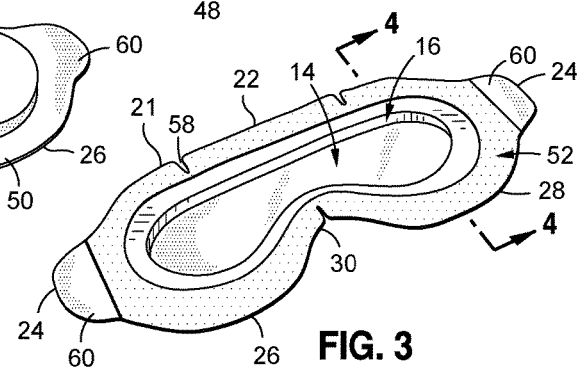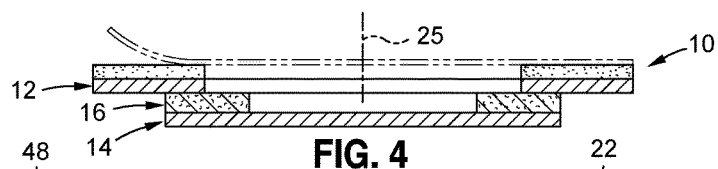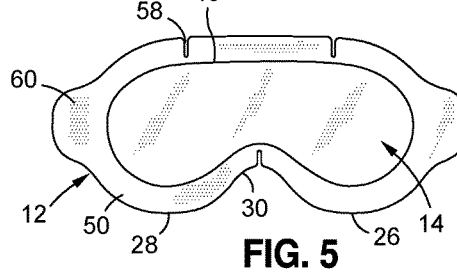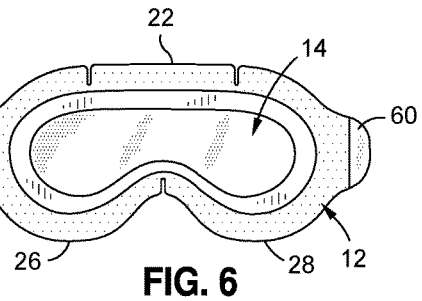

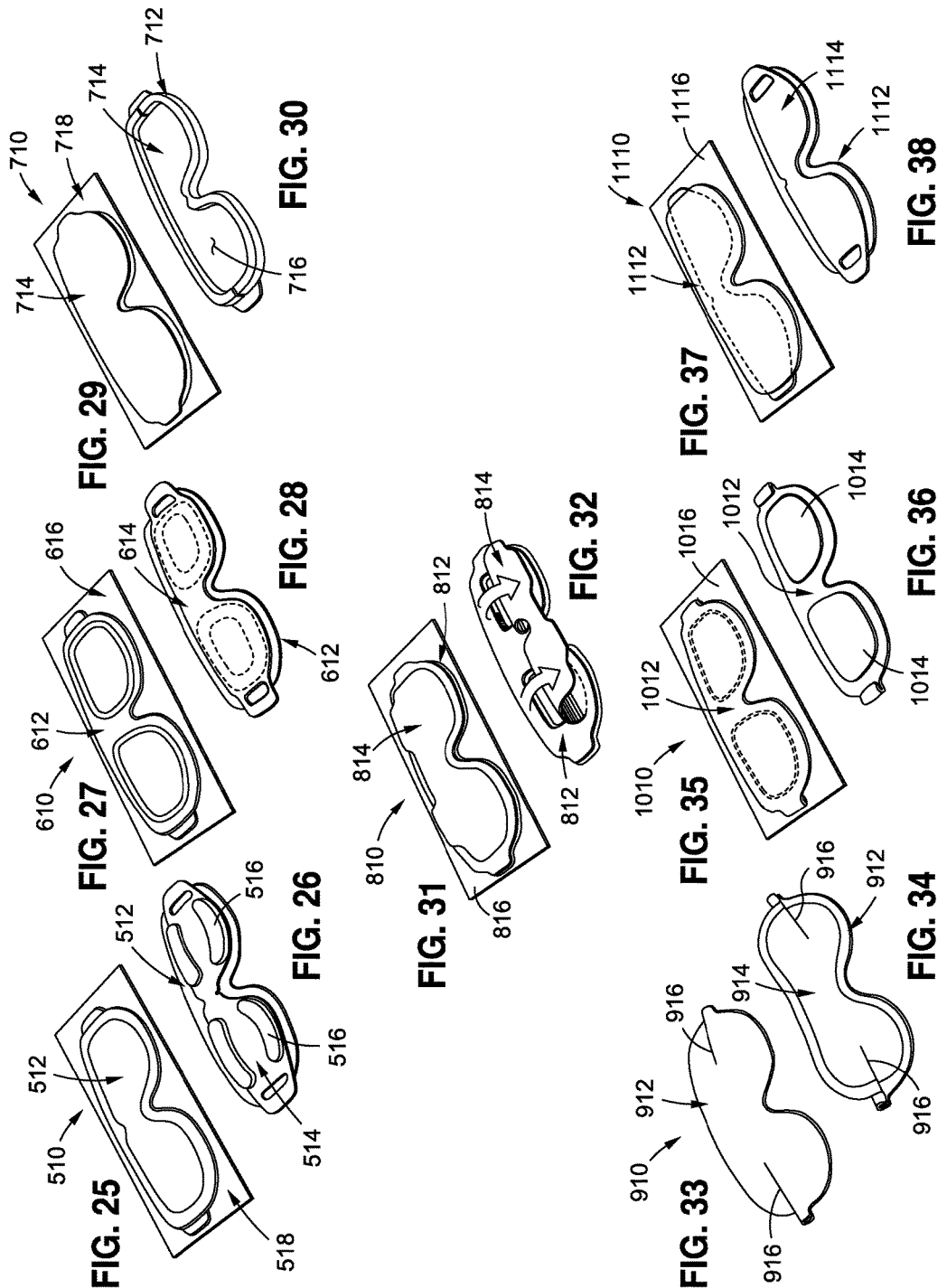

SLEEP MASK APPARATUS

CROSS-REFERENCE TO RELATED APPLICATIONS

Not Applicable
STATEMENT RE: FEDERALLY SPONSORED RESEARCH/DEVELOPMENT
Not Applicable

BACKGROUND OF THE INVENTION

1. Field of the Invention

The present invention relates generally to a sleep mask, and more specifically, to a disposable sleep mask designed to enhance the overall comfort to the user.

2. Description of the Related Art

Most people achieve more restful sleep in dark environments. Along these lines, there are various health-related reasons as to why humans are adapted to sleep in the dark. The absence of light is known to induce many beneficial biochemical changes in humans. For instance, in dark environments, humans generally produce higher levels of melatonin, which is a critical hormone associated with several biological functions.

Despite the beneficial effects of sleeping in a dark environment, the modern world has made it difficult to sleep in a truly dark environment. When night falls, it is common to turn lights on or watch television, which is disruptive to one's natural circadian rhythm. Consequently, humans may suffer from inadequate and restful sleep. This results in a population that is chronically and dangerously sleep deprived, with resulting fatigue, irritability, depression, impaired reflexes, and susceptibility to accidents. Those who work the night shift are even more susceptible to the aforementioned problems. Furthermore, the elderly are particularly prone to sleep disorders, because their ability to produce melatonin decreases sharply with age. Moreover, those who suffer from certain diseases, such as Alzheimer's, experience severe disruptions in their sleep/wake cycle.

Recognizing the problems associated with light effecting one's ability to sleep, several prior art sleep masks have been developed for shielding a user's eyes from light. Conventional sleep masks are typically made of cloth or synthetic fiber and are generally intended for more than one use. Such sleep masks are often held in place with elastic bands or straps that wrap behind the user's head and attach with means such as hook and loop material, snaps, buttons, etc. Oftentimes, the materials used in these currently available sleep masks do not completely block out all light and therefore may not replicate the effects of a completely dark environment, which may be needed for restful sleep. Also, skin and/or scalp irritation may be caused by the materials used in the bands or straps that hold the mask on the user's head. Moreover, an uncomfortable sensation of pressure on the face or head may result from the tension created by the elastic bands or straps behind the head. The bands or strap may also alter the contact point of the head with the sleeping surface, such as the pillow or mattress.

Accordingly, there is a need in the art for a disposable sleep mask that is more comfortable than conventional sleep masks. Various aspects of the present invention address this particular need, as will be discussed in more detail below.

BRIEF SUMMARY OF THE INVENTION

In accordance with one embodiment of the present invention, there is provided a disposable sleep mask which is specifically configured and adapted to be attached to the user's head without the use of a strap or band.

According to one embodiment, there is provided a sleep mask apparatus for use over a user's eyes. The sleep mask apparatus includes an opaque element having an inner surface and an opposing outer surface. The opaque element is sized and configured to extend across both of the user's eyes to mitigate the passage of light toward the user's eyes, with the inner surface facing the user and the outer surface facing away from the user. A support element is coupled to the opaque element and includes a first support surface and an opposing second support surface. The inner surface of the opaque element is offset from the first support surface. The support element defines a peripheral margin extending around the opaque element, with the first support surface having an adhesive applied thereto at the peripheral margin to facilitate adhering of the support element to the user.

The support element may define an opening, with the opaque element extending over the opening and being spaced from the support element. The sleep mask may further comprise a spacer disposed between the support element and the opaque element. The spacer may be fabricated from a foam material.

The support element may include at least one opening and the opaque element may include a cup element defining a substantially concave surface and an opposing substantially convex surface, with the cup element extending over the at least one opening.

The support element may include a pair of openings and the opaque element may include a pair of cup elements. Each cup element may define a substantially concave surface and an opposing substantially convex surface. The pair of cup elements may extend over respective ones of the pair of openings.

The opaque element and the support element may be fused together to form an integral structure having a cavity surrounded by the peripheral margin.

The support element may include an opening and the opaque element may be selectively transitional relative to the support element between an open position and a closed position. The opening may include a pair of openings, and the opaque element may include a pair of opaque regions, wherein each opaque region may be operatively associated with a respective one of the pair of openings. Each opaque region may be independently transitional between the open and closed positions.

The support element may include a non-adhesive region extending radially outward from the peripheral margin.

The support element may include at least one slit formed within the peripheral margin.

The peripheral contour of the support element may include a nose section to accommodate the anatomy of the user's nose.

The adhesive applied to the support element may completely surround the opaque element. The adhesive may extend radially outward relative to the opaque element.

According to another embodiment, there is provided a sleep mask apparatus for covering a user's eyes. The sleep mask apparatus may include a main body having an opaque region and an adhesive region circumnavigating the opaque region. The opaque region may include an inner surface, and may be configured to mitigate the passage of light therethrough, and wherein the adhesive region may include a first adhesive surface. The main body is configured to extend over both of the user's eyes. The inner surface of the opaque region and the first adhesive surface face the user when the main body is extended over the user's eyes, with the first adhesive surface being axially offset from the inner surface of the opaque region.

The present invention will be best understood by reference to the following detailed description when read in conjunction with the accompanying drawings.

BRIEF DESCRIPTION OF THE DRAWINGS

These and other features and advantages of the various embodiments disclosed herein will be better understood with respect to the following description and drawings, in which:

FIG. 1 is a side view of a first embodiment of a sleep mask apparatus covering a user's eyes;

FIG. 2 is a front perspective view of the first embodiment of the sleep mask apparatus;

FIG. 3 is a rear perspective view of the sleep mask apparatus depicted in FIG. 2;

FIG. 4 is a side sectional view of the sleep mask apparatus depicted in FIG. 3;

FIG. 5 is a front view of the sleep mask apparatus depicted in FIG. 2;

FIG. 6 is a rear view of the sleep mask apparatus depicted in FIG. 2;

FIG. 7 is an exploded rear perspective view of the sleep mask apparatus depicted in FIG. 2;

FIGS. 25 and 26 depict a sixth embodiment of a sleep mask apparatus;

FIGS. 27 and 28 depict a seventh embodiment of a sleep mask apparatus;

FIGS. 29 and 30 depict an eighth embodiment of a sleep mask apparatus;

FIGS. 31 and 32 depict a ninth embodiment of a sleep mask apparatus;

FIGS. 33 and 34 depict a tenth embodiment of a sleep mask apparatus;

FIGS. 35 and 36 depict an eleventh embodiment of a sleep mask apparatus; and

FIGS. 37 and 38 depict a twelfth embodiment of a sleep mask apparatus.

Common reference numerals are used throughout the drawings and the detailed description to indicate the same elements.

DETAILED DESCRIPTION OF THE INVENTION

Figure 8:
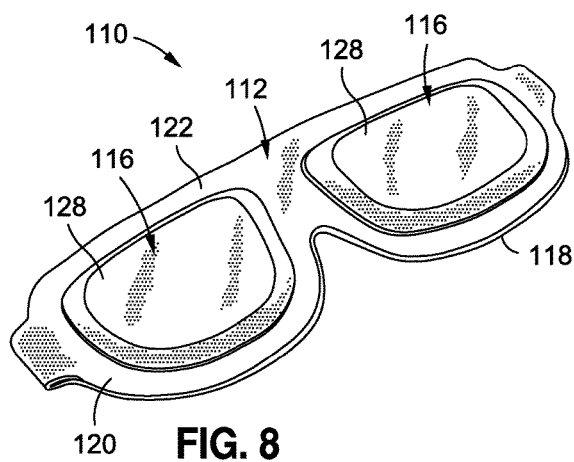
FIG. 8 is a front perspective view of a second embodiment of a sleep mask apparatus including a support element and a pair of cup members.

The detailed description set forth below in connection with the appended drawings is intended as a description of certain embodiments of an apparatus for a sleep mask and is not intended to represent the only forms that may be developed or utilized. The description sets forth the various structure and/or functions in connection with the illustrated embodiments, but it is to be understood, however, that the same or equivalent structure and/or functions may be accomplished by different embodiments that are also intended to be encompassed within the scope of the present disclosure. It is further understood that the use of relational terms such as first and second, and the like are used solely to distinguish one entity from another without necessarily requiring or implying any actual such relationship or order between such entities.

Various aspects of the present invention are directed toward a disposable sleep mask that can be quickly and easily placed over the user's eyes for blocking light. The sleep mask apparatus generally includes a main body having an opaque region and an adhesive region circumnavigating the opaque region. The adhesive region is used for adhering the sleep mask apparatus to the user, while the opaque region is specifically configured and adapted to mitigate the passage of light therethrough.

Referring now specifically to FIGS. 1-7, there is depicted a first embodiment of a sleep mask 10 including a support element 12, an opaque element 14, and a spacer 16 disposed between the support element 12 and the opaque element 14. Those skilled in the art will recognize that the spacer 16 may be referred to as an intermediate member or an intermediate region of the main body by virtue of the spacer 16 being disposed between the support element 12 and the opaque element 14.

According to one embodiment, the support element 12 is an annular flexible member including a first support surface 18 and an opposing second support surface 20. When the sleep mask 10 is worn by the user, the first support surface 18 faces the user, and the second support surface 20 faces away from the user. The support element 12 is formed from a flexible material that is capable of conforming to the anatomy of the user's face. According to one embodiment, the support element 12 is formed from a spunbond material, although other materials known in the art can also be used. The support element 12 includes an outer periphery 21 that includes a forehead segment 22, a pair of opposed side segments 24, a first cheek segment 26, a second cheek segment 28, and a nose segment 30 interposed between the first and second cheek segments 26, 28. In the embodiment depicted in FIGS. 1-7, the support element 12 also includes an inner periphery 32, e.g., a support inner periphery (see FIG. 7) which defines a central opening 34. The inner periphery 32 is sized to extend around both of the user's eyes, such that the user's eyelids and or eyelashes may protrude through the opening 34 when the sleep mask 10 is worn by the user. The inner periphery 32 generally conforms to the configuration of the outer periphery 21. The support element 12 may be die-cut, stamped or formed using other techniques known by those skilled in the art.

The spacer 16 is coupled to support element 12 and includes a first spacer surface 36 and an opposing second spacer surface 38. The first spacer surface 36 is coupled to the second support surface 20, such that the spacer 16 extends away from the user when the sleep mask 10 is attached to the user. The spacer 16 is an annular structure and includes a spacer outer periphery 39 and a spacer inner periphery 40. The spacer inner periphery 40 defines a spacer opening 42 that is in communication with the support element opening 34. In other words, the spacer opening 42 overlaps the support element opening 34. The spacer 16 is sized and configured such that the spacer outer periphery 39 is disposed inward of the support element outer periphery 21 (e.g., the support element outer periphery 21 circumnavigates the spacer outer periphery 39), and the spacer inner periphery 40 is either flush with the support element inner periphery 32, or set slightly outwardly offset of the support element inner periphery 32 (e.g., the spacer inner periphery 40 may circumnavigate the support element inner periphery 32). The spacer 16 may be fabricated from foam or other similar materials which may not be as flexible as the support element 12. In this regard, the support element 12 is sized and configured to protrude radially outward from the spacer 16 to provide a flexible border that is capable of conforming to the user's facial contours. However, the spacer 16 is pliant and has a degree of flexibility which allows the sleep mask 10 to bend around the front of the user's face, as shown in FIG. 1.

The opaque element 14 includes a first opaque surface 44 (e.g., an inner surface) and an opposing second opaque surface 46 (e.g., an outer surface), with the first opaque surface 44 being coupled to the spacer second surface 38. The opaque element 14 is sized and configured to extend across both of the user's eyes to mitigate the passage of light toward the user's eyes. In this respect, the opaque element 14 extends over the support element opening 34, and the spacer opening 42. Furthermore, the opaque element 14 is formed from an opaque, light blocking material, such as flocked paper, athletic tape, metallic foil laminated on paper, multiple layers of medium weight (approximately 65 gsm) spunbond, or other light-blocking materials known in the art. The opaque element 14 includes an opaque outer periphery 48 that is at least equal to the spacer inner periphery 40 so that the opaque element 14 covers the spacer opening 42.

The sleep mask 10 is specifically configured and adapted to cover the eyes of the user, while at the same time, providing a space over the user's eyes to enhance the comfort of the sleep mask 10 when worn by the user. In this regard, the user's eyelids or eyelashes may not be compressed by the sleep mask 10, despite the presence of the sleep mask 10 on the user's face. Instead, the eyelids or eyelashes may extend into the support element opening 34 and spacer opening 42. Furthermore, depending on the thickness of the spacer 16, and the associated depth of the spacer opening 42, the user may be able to blink when wearing the sleep mask 10.

The space, i.e., a void, over the user's eyes results in the first opaque surface 44 being offset from the first support surface 18. In particular, the first opaque surface 44 is offset from first support surface 18 along an axis 25 that is generally perpendicular to the first support surface 18 when the first support surface 18 is in a generally planar orientation (e.g., see FIG. 4). In this respect, in the embodiment of the sleep mask 10 depicted in FIGS. 1-7, the first opaque surface 44 does not reside in the same plane as the first support surface 18.

The support element 12 defines a peripheral margin extending around the spacer 16 and opaque element 14. The first support surface 18 includes an adhesive 52 applied thereto at the peripheral margin 50 to facilitate adhering of the support element 12 to the user. The adhesive 52 includes an adhesive inner periphery 54 which may be spaced from the support element inner periphery 32. In this regard, the first support surface 18 may include an adhesive region defined by the adhesive 52, and an inner, non-adhesive region disposed between the adhesive 52 and the support element opening 34. The adhesive 52 may be die-cut or partially exposed adhesive, or other adhesive elements known by those skilled in the art.

The sleep mask 10 may additionally include a peel-away liner 56 which covers the adhesive 52 until the sleep mask 10 is ready to be used. At that time, the peel-away liner 56 may be removed to expose the adhesive 52 for securing the sleep mask 10 to the user's face.

The support element 12 may include at least one slit 58 formed within the peripheral margin 50. The slit(s) 58 allow the support element 12 to bend or flex for conforming to the contours of the user's face.

The support element 12 may further include a pair of lateral tabs 60 positioned outwardly from the adhesive 52. The tabs 60 may include a non-adhesive region on the support element first surface 18. The tabs 60 are configured and adapted to allow the user to manually hold and manipulate the sleep mask 10 without interfering with the adhesive 52.

Figure 10:
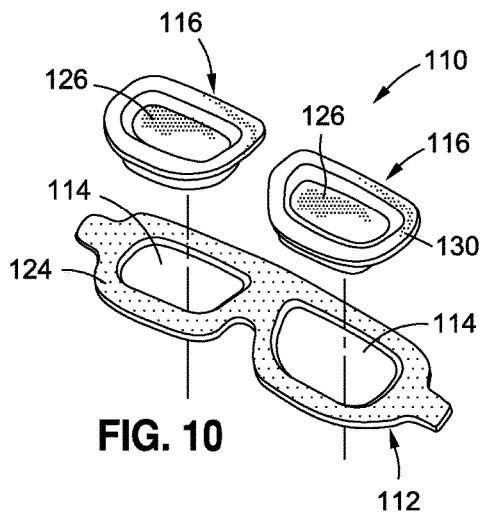
FIG. 10 is an exploded rear perspective view of the sleep mask apparatus depicted in FIG. 8.
Figure 9:
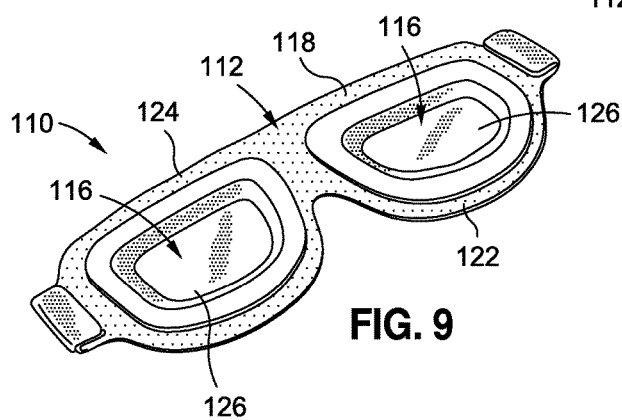
FIG. 9 is a rear perspective view of the sleep mask apparatus depicted in FIG. 8.

Referring now to FIGS. 8-10, there is depicted another embodiment of a sleep mask 110 including a support element 112 having a pair of openings 114 and a pair of opaque cup elements 116 disposed within respective ones of the openings 114 for covering the openings 114. In this respect, the support element 112 essentially acts as a frame for supporting the pair of cup elements 116.

The support element 112 includes a first support surface 118 which faces the user and a second support surface 120 which faces away from the user. The outer periphery of the support element 112 similar to the outer periphery of the support element 12 discussed above. In the exemplary embodiment, the support element 112 completely surrounds each opaque cup element 116 to define a peripheral margin 122 around the opaque cup elements 116. An adhesive 124 is applied to the first support surface 118 for adhering the sleep mask 110 to the user.

Each opaque cup element 116 defines a substantially concave inner surface 126 and an opposing substantially convex outer surface 128. The inner surface 126 faces the user when the mask 110 is worn by the user. The concave configuration of the inner surface 126 creates a space over the user's eyes during use. The opaque cup elements 116 may be thermoformed paper cups which are formed from an opaque material. Each cup element 116 may also include a flange portion 130 which extends around the concave inner surface 126 and is adapted to interface with the support element 112 when the cup elements 116 are coupled to the support element 112. In particular, the flange portion 130 may abut against the first support surface 118 to prevent the cup element 116 from passing through the openings 114. The cup elements 116 may be coupled to the support surface 112 using an adhesive or other fastening elements known in the art.

Figure 11:
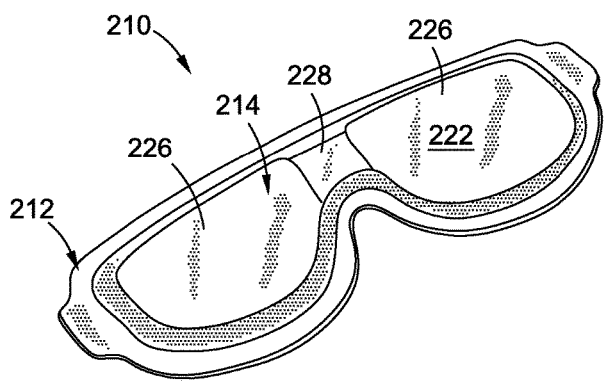
FIG. 11 is a front perspective view of a third embodiment of a sleep mask apparatus.
Figure 12:
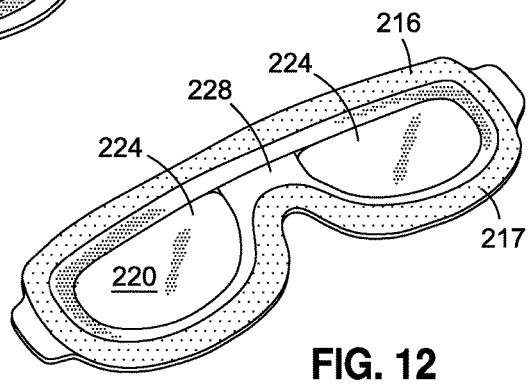
FIG. 12 is a rear perspective view of the sleep mask apparatus depicted in FIG. 11.
Figure 13:
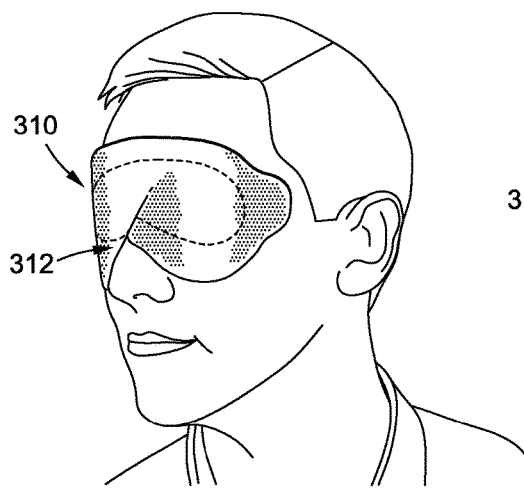
FIG. 13 is a front perspective view of a fourth embodiment of a sleep mask apparatus shown covering a user's eyes.
Figure 14:
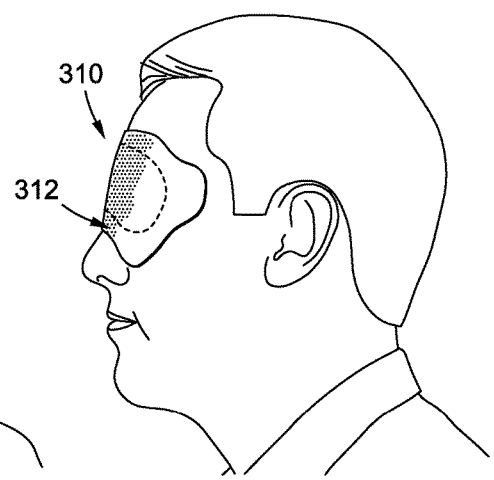
FIG. 14 is a side view of the sleep mask apparatus and user depicted in FIG. 13.
Figure 15:
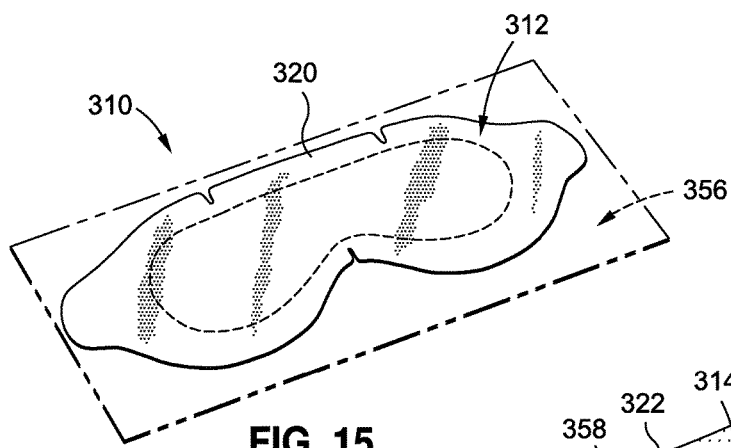
FIG. 15 is a front perspective view of the fourth embodiment of the sleep mask apparatus.
Figure 16:
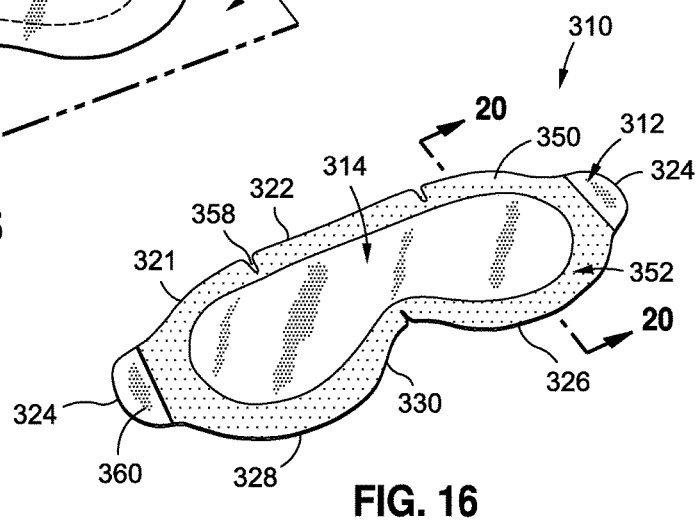
FIG. 16 is a rear perspective view of the sleep mask apparatus depicted in FIG. 15.
Figure 19:
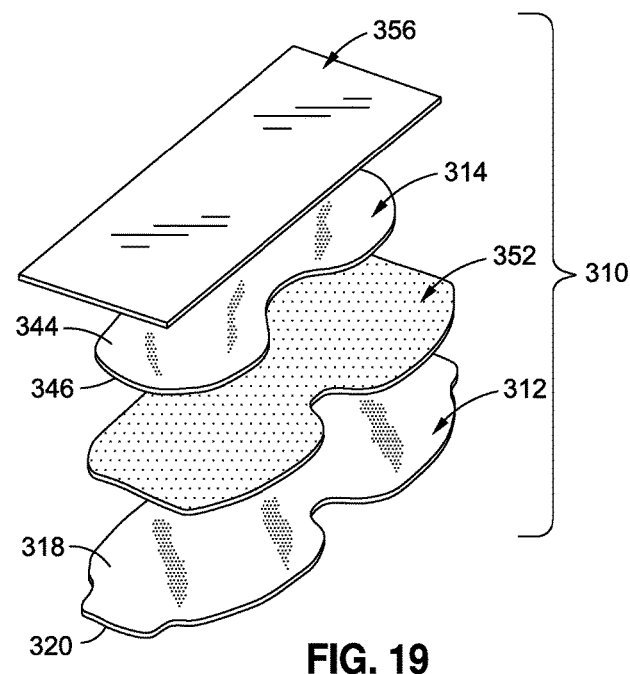
FIG. 19 is an exploded rear perspective view of the sleep mask apparatus depicted in FIG. 15.
Figure 17:
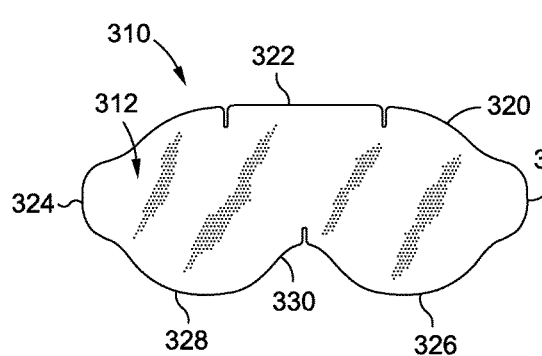
FIG. 17 is a front view of the sleep mask apparatus depicted in FIG. 15.
Figure 18:
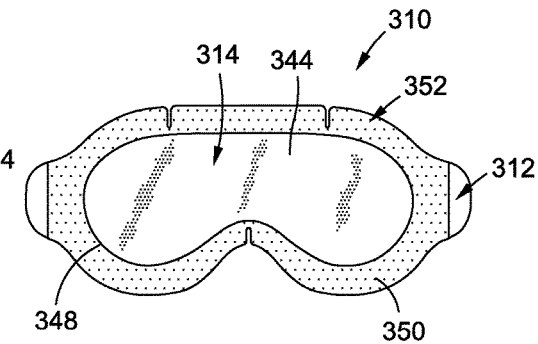
FIG. 18 is a rear view of the sleep mask apparatus depicted in FIG. 15.
Figure 20:
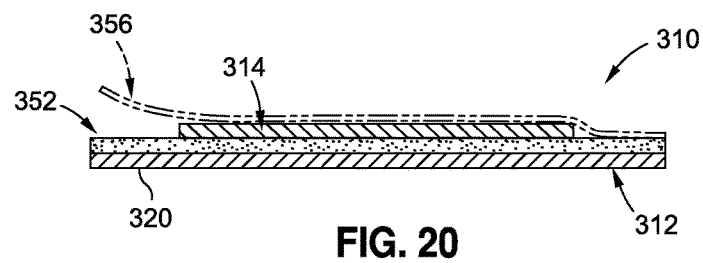
FIG. 20 is a side sectional view of the sleep mask apparatus depicted in FIG. 15.

Referring now to FIGS. 11-12, there is depicted a third embodiment of a sleep mask 210 that is similar to the second embodiment of the sleep mask 110 described above. The primary distinction between the mask 210 and the mask 110 is that the entire mask 210 is thermoformed. In this regard, the mask 210 includes a peripheral support element 212 surrounding a central opaque element 214. The peripheral support element 212 includes a first support surface 216 and an opposing second support surface 218, wherein the first support surface 216 faces the user when the mask 210 is worn. The first support surface 216 may include an adhesive 217 disposed thereon to effectuate adhering of the sleep mask 210 to the user's face. The peripheral support element 212 may also be flexible to adapt to the contour of the user's face.

The central opaque element 214 includes a first opaque surface 220 and an opposing second opaque surface 222. The central opaque element 214 includes a pair of concave regions 224 and a pair of corresponding convex regions 226. The concave and convex regions 224, 226 may be separated by a ridge 228, which also extends from opposed portions of the peripheral support element 212. The concave regions 224 define a cavity that is surrounded by the peripheral support element 212. The cavity provides a space over the user's eyes when the sleep mask 210 is worn to enhance the overall comfort of wearing the mask 210.

Referring now to FIGS. 13-20, there is depicted a fourth embodiment of a sleep mask 310, which generally includes a support element 312, and an opaque element 314. The sleep mask 310 is configured similar to an adhesive bandage, in that the support element 312 is flexible and includes an adhesive for adhering the sleep mask 310 to the user, and acts as a carrier for the centrally located opaque element 314, which is adapted to mitigate the passage of light toward the user's eyes. In this respect, the sleep mask 310 is specifically configured and adapted such that the opaque element 314 is positioned between the user and the support element 312 when the mask 310 is worn by the user.

The support element 312 includes a first support surface 318 and an opposing second support surface 320. When the sleep mask 310 is worn by the user, the first support surface 318 faces the user, and the second support surface 320 faces away from the user. The support element 312 is formed from a flexible material that is capable of conforming to the anatomy of the user's face. According to one embodiment, the support element 312 is formed from a spunbond material, although other materials known in the art can also be used. The support element 312 includes an outer periphery 321 that includes a forehead segment 322, a pair of opposed side segments 324, a first cheek segment 326, a second cheek segment 328, and a nose segment 330 interposed between the first and second cheek segments 326, 328. The support element 312 may be die-cut, stamped or formed using other techniques known by those skilled in the art.

The opaque element 314 includes a first opaque surface 344 and an opposing second opaque surface 346, with the second opaque surface 346 being coupled to the first support surface 318. The opaque element 314 is sized and configured to extend across both of the user's eyes to mitigate the passage of light toward the user's eyes. Furthermore, the opaque element 314 is formed from an opaque, light blocking material, such as flocked paper, athletic tape, metallic foil laminated on paper, multiple layers of medium weight (approximately 65 gsm) spunbond, or other light-blocking materials known in the art. The opaque element 314 includes an opaque outer periphery 348 that may reside inwardly from the support element outer periphery 321 to define a peripheral margin 350 between the opaque outer periphery 348 and the support element outer periphery 321.

The first support surface 318 includes an adhesive 352 applied thereto at the peripheral margin 350 to facilitate adhering of the support element 312 to the user. The adhesive 352 may be die-cut or partially exposed adhesive, or other adhesive elements known by those skilled in the art. It is also contemplated that the adhesive 350 may extend between the opaque element 314 and the support element 312 for coupling the opaque element 314 to the support element 312.

The sleep mask 310 may additionally include a peel-away liner 356 which covers the adhesive 352 until the sleep mask 310 is ready to be used. At that time, the peel-away liner 356 may be removed to expose the adhesive 352 for securing the sleep mask 310 to the user's face.

The support element 312 may include at least one slit 358 formed within the peripheral margin 350. The slit(s) 358 allow the support element 312 to bend or flex for conforming to the contours of the user's face.

The support element 312 may further include a pair of lateral tabs 360 positioned outwardly from the adhesive 352. The tabs 360 may include a non-adhesive region on the support element first surface 318. The tabs 360 are configured and adapted to allow the user to manually hold and manipulate the sleep mask 310 without interfering with the adhesive 352.

Figure 21:
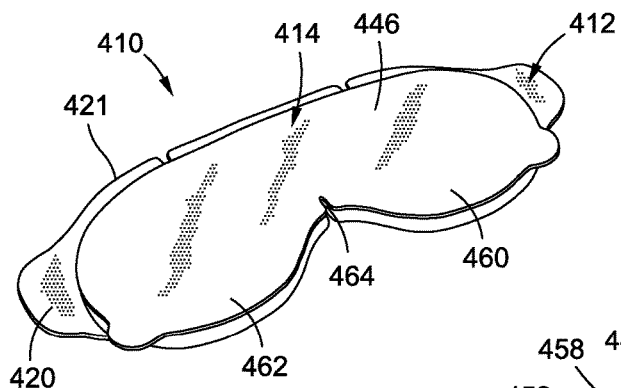
FIG. 21 is an upper front perspective view of a fifth embodiment of a sleep mask apparatus having opaque flaps.

Referring now to FIGS. 21-24, there is depicted a fifth embodiment of a sleep mask 410 generally including a support element 412 and an opaque element 414 that is specifically configured and adapted to be selectively transitional relative to the support element 412 between an open position (see FIG. 24) and a closed position (see FIG. 21). In this respect, the user wearing the sleep mask 410 may transition the opaque element 414 to the open position for viewing through the sleep mask 410, rather than having to completely remove the sleep mask 410.

The sleep mask 410 is very similar to the sleep mask 10 described above, with the primary distinction being the ability of the opaque element 414 to transition between the open and closed positions. Therefore, the following discussion will focus on the unique features of the sleep mask 410, and for a more comprehensive discussion of those features that are shared with the sleep mask 10, please refer to the previous discussion.

The support element 412 includes a first support surface 418 and an opposing second support surface 420. When the sleep mask 410 is worn by the user, the first support surface 418 faces the user, and the second support surface 420 faces away from the user. The support element 412 includes an outer periphery 421 and an inner periphery which defines a central opening 434. The inner periphery is sized to extend around both of the user's eyes, such that the user's eyelids and or eyelashes may protrude through the opening 434 when the sleep mask 410 is worn by the user. The support element 412 shown in FIG. 22 includes a single central opening 434, although it is understood that the support element 412 may include a pair of central openings adapted to extend around respective ones of the user's eyes. The first support surface 418 includes an adhesive 452 applied thereto to facilitate adhering of the support element 412 to the user.

The support element 412 may include at least one slit 458 formed therein to allow the support element 412 to more easily flex or bend.

The spacer 416 is coupled to support element 412 and includes a first spacer surface 436 and an opposing second spacer surface. The first spacer surface 436 is coupled to the second support surface 420, such that the spacer 416 extends away from the user when the sleep mask 410 is attached to the user. The spacer 416 includes a spacer outer periphery 439 and a pair of spacer openings 442, 443 extending between the first and second spacer surfaces 436, 438 and in communication with the support element opening 434.

The opaque element 414 includes a first opaque surface 444 and an opposing second opaque surface 446, with the first opaque surface 444 being coupled to the spacer second surface 438. The opaque element 414 is sized and configured to extend across both of the user's eyes to mitigate the passage of light toward the user's eyes. In this respect, the opaque element 414 extends over the support element opening 434, and the spacer openings 442, 443. The opaque element 414 includes a first flap portion 460 extending over a first spacer opening 442 and a second flap portion 462 extending over a second spacer opening 443. The flap portions 460, 462 may be separated by a slit 464, which allows the flap portions 460, 462 to more easily transition between the open and closed positions separately. In the exemplary embodiment, the first flap portion 460 and second flap portion 462 are formed from a single piece of material, although it is understood that in other embodiments the first and second flap portions 460, 462 may be formed of separate pieces of material.

Figure 22:
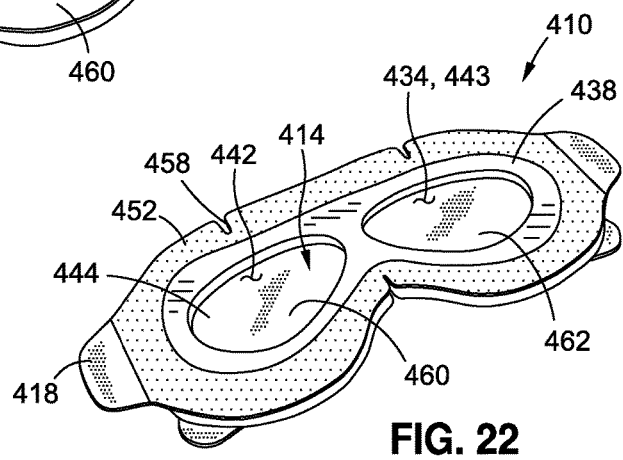
FIG. 22 is a rear perspective view of the sleep mask apparatus depicted in FIG. 21.
Figure 23:
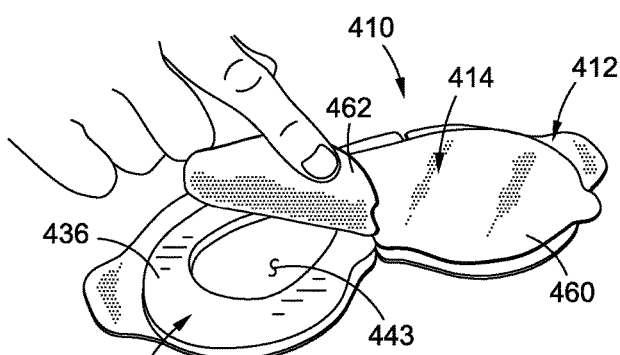
FIG. 23 is an upper front perspective view of the sleep mask apparatus depicted in FIG. 21, with one flap in an open position and another flap in a closed position.
Figure 24:
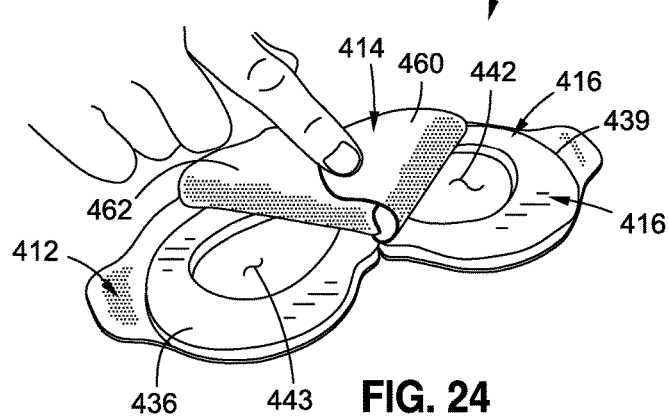
FIG. 24 is an upper front perspective view of the sleep mask apparatus depicted in FIG. 21, with both flaps in the open position.

As shown in FIGS. 21 and 22, both flaps portions 460, 462 are in the closed position, with each flap portion 460, 462 extending over the corresponding spacer opening 442, 443 (e.g., the first flap portion 460 extends over the first spacer opening 442, while the second flap portion 462 extends over the second spacer opening 443). FIG. 23 shows the second flap portion 462 in an open position and the first flap portion 460 in the closed position. In particular, the second flap portion 462 has been moved away from the spacer 416 to uncover the second spacer opening 443, while the first flap portion 460 remains over the first spacer opening 442. FIG. 24 shows both flap portions 460, 462 in the open position, with each flap portion 460, 462 being moved away from the spacer 416 to uncover the corresponding spacer openings 442, 443.

Referring now to FIGS. 25-38, there is shown several alternative embodiments of the sleep mask. FIGS. 25-26 show a sixth embodiment of a sleep mask 510, with FIG. 25 showing a front perspective view and FIG. 26 showing a rear perspective view. The sleep mask 510 includes a support element 512, an opaque element 514 coupled to the support element 512, and a plurality of pads 516 coupled to the opaque element 514. FIG. 25 also shows a tear-away liner 518, coupled to the support element 512. The pads 516 are positioned such that the pads 516 engage with user around the user's eyes, without covering the eyes. In this respect, the pads 516 space the opaque element 514 away from the user's eyes to create a gap between the user's eyes and the opaque element 514 when the mask 510 is worn by the user. In order to account for the gap, while at the same time being able to engage with the user's face, the support element 512 may include a raised central region relative to an outer peripheral region.

Turning now to FIGS. 27-28, there is depicted a seventh embodiment of a sleep mask 610, with FIG. 27 showing a front perspective view and FIG. 28 showing a rear perspective view. The mask 610 includes a support element 612 and an opaque element 614 coupled to the support element 612. The opaque element 614 is adapted to be positioned between the support element 612 and the user's face when the mask 610 is worn by the user. The opaque element 614 defines a pair of cavities which may be placed over the user's eyes when the mask 610 is worn. The opaque element 614 may be thermoformed or formed using other techniques known in the art. FIG. 27 shows a tear-away liner 616 coupled to the support element 612.

FIGS. 29-30 show an eighth embodiment of a sleep mask 710 including an annular, peripheral support element 712 (e.g., a peripheral wall), and an opaque element 714 coupled to the support element 712 and extending over an opening 716 defined by the support element 712. FIG. 29 is a front perspective view and FIG. 30 is a rear perspective view. The sleep mask 710 is configured such that the peripheral support element 712 engages with the user's face and extends around both of the user's eyes. The support element 712 is of a sufficient thickness so as to provide a space between the user's eyes and the opaque element 714. FIG. 29 shows a tear-away liner 718 coupled to the support element 712.

FIGS. 31 and 32 depict a ninth embodiment of a sleep mask 810 having a support element 812 and an opaque element 814 configured to be selectively transitional relative to the support element 812 between open and closed positions. FIG. 31 is a front perspective view with the opaque element 814 in the closed position and FIG. 32 is a front perspective view with the opaque element 814 moved toward the open position. The support element 812 defines a pair of openings which are covered by the opaque element 814 when the opaque element 814 is in the closed position, and uncovered by the opaque element 814 when the opaque element 814 is in the open position. FIG. 31 shows a tear-away liner 816 coupled to the support element 812.

A tenth embodiment of the sleep mask 910 is shown in FIGS. 33 and 34 and includes a support element 912 and an opaque element 914. FIG. 33 is a front perspective view and FIG. 34 is a rear perspective view. The mask 910 further includes a pair of slits 916 extending through the support element 912 and opaque element 914 from opposing lateral portions of the mask 910. The slits 916 allow the mask 910 to assume an arched profile to create space between the user's eyes and the opaque element 914.

FIGS. 35 and 36 show yet another embodiment of the sleep mask 1010, which includes a support element 1012 and a pair of opaque elements 1014 coupled to the support element 1012. FIG. 35 is a front perspective view and FIG. 36 is a rear perspective view. The pair of opaque elements 1014 are shaped similar to lenses in a conventional pair of glasses. The opaque elements 1014 are configured to reside between the user and the support element 1012 and over the user's eyes during use of the sleep mask 1010. The opaque elements 1014 may be fabricated from a soft, comfortable material, such as foam. FIG. 35 shows a tear-away liner 1016 coupled to the support element 1012.

FIGS. 37 and 38 depict a further embodiment of the sleep mask 1110, which includes a support element 1112 and an opaque element 1114 coupled to the support element 1112. FIG. 37 is a front perspective view and FIG. 38 is a rear perspective view. The mask 1110 shown in FIGS. 37 and 38 is similar to the mask 1010 depicted in FIGS. 35 and 36, with the primary distinction being the configuration of the opaque element 1114. In particular, the mask 1110 includes a unitary opaque element 1114 which is configured to extend over both eyes, whereas the mask 1010 includes separate opaque elements 1014 for each eye. FIG. 37 shows a tear-away liner 1116 coupled to the support element 1112.

It is contemplated that the sleep masks described above may be adapted to accommodate both large heads and small heads, and thus, the sleep masks may be manufactured as "one-size fits all." However, it is also contemplated that the masks may be made in multiple sizes, without departing from the spirit and scope of the present invention.

Furthermore, it is further understood that logos, symbols, wording, any alphanumeric character(s) or other indicia may be imprinted or emblazoned anywhere on the sleep mask.

The particulars shown herein are by way of example only for purposes of illustrative discussion, and are not presented in the cause of providing what is believed to be most useful and readily understood description of the principles and conceptual aspects of the various embodiments of the present disclosure. In this regard, no attempt is made to show any more detail than is necessary for a fundamental understanding of the different features of the various embodiments, the description taken with the drawings making apparent to those skilled in the art how these may be implemented in practice.

What is claimed is:

1. A sleep mask apparatus for use over a user's eyes, the sleep mask apparatus comprising:
   an opaque element having an outer periphery, an inner surface, and an opposing outer surface, the opaque element being sized and configured to extend across both of the user's eyes to mitigate the passage of light toward the user's eyes with the inner surface facing the user and the outer surface facing away from the user;
   a support element having an outer periphery extending around an axis, a first surface and an opposing second surface, the inner surface of the opaque element being axially offset along the axis from the first surface of the support element, the support element defining a peripheral margin extending around the opaque element, the first surface having an adhesive applied thereto at the peripheral margin to facilitate adhering the support element to the user; and
   a spacer having a first surface and an opposing second surface, the spacer being disposed between the opaque element and the support element such that the first surface of the spacer is coupled to the support element and the second surface of the spacer is coupled to the opaque element, the spacer having an outer periphery radially offset from the outer periphery of the support element and positioned inwardly from the outer periphery of the support element;
   the outer periphery of the support element being spaced outward from the outer periphery of the opaque element to define the peripheral margin;
   the opaque element, the support element, and the spacer collectively defining a void extending from the first surface of the support element to the inner surface of the opaque element, the void being placeable over the user's eyes such that at least a portion of the user's eyelids protrude into the void.

2. The sleep mask apparatus recited in claim 1, wherein the support element defines an opening, the opaque element extending over the opening and being spaced from the support element.

3. The sleep mask apparatus recited in claim 1, wherein the spacer is fabricated from a foam material.

4. The sleep mask apparatus recited in claim 1, wherein the support element includes at least one opening and the opaque element includes a cup element defining a substantially concave surface and an opposing substantially convex surface, the cup element extending over the at least one opening.

5. The sleep mask apparatus recited in claim 1, wherein the support element includes a pair of openings and the opaque element includes a pair of cup elements, each cup element defining a substantially concave surface and an opposing substantially convex surface, the pair of cup elements extending over respective ones of the pair of openings.

6. The sleep mask apparatus recited in claim 1, wherein the opaque element and the support element are fused together to form an integral structure.

7. The sleep mask apparatus recited in claim 1, wherein the support element includes an opening and the opaque element is selectively transitional relative to the support element between an open position and a closed position.

8. The sleep mask apparatus recited in claim 7, wherein the opening includes a pair of openings, the opaque element including a pair of opaque regions, each opaque region being operatively associated with a respective one of the pair of openings.

9. The sleep mask apparatus recited in claim 8, wherein each opaque region is independently transitional between the open and closed positions.

10. The sleep mask apparatus recited in claim 1, wherein the support element includes a non-adhesive region extending outward from the peripheral margin.

11. The sleep mask apparatus recited in claim 1, wherein the support element includes at least one slit formed within the peripheral margin.

12. The sleep mask apparatus recited in claim 1, wherein a peripheral contour of the support element includes a nose section to accommodate the anatomy of the user's nose.

13. The sleep mask apparatus recited in claim 1, wherein the adhesive completely surrounds the opaque element.

14. The sleep mask apparatus recited in claim 1, wherein the adhesive extends outward relative to the opaque element.

15. A sleep mask apparatus for covering a user's eyes, the sleep mask apparatus comprising:
   a main body having an opaque region defining an outer periphery, an adhesive region defining an outer periphery, and a spacer disposed between the opaque region and the adhesive region and having an inner periphery defining an opening and an outer periphery offset from the outer periphery of the adhesive region and positioned inwardly from the outer periphery of the adhesive region, at least a portion of the adhesive region is spaced from the outer periphery of the opaque region and circumnavigates the opaque region, the opaque region having an inner surface, and being configured to mitigate the passage of light therethrough, the adhesive region having a first surface;
   the main body defining a void extending from the inner surface of the opaque region toward the adhesive region, the void being sized and structured to be placeable over both of the user's eyes to provide a space over the user's eyes when the sleep mask apparatus is worn by a user such that at least a portion of the user's eyelids protrude into the void;
   the inner surface of the opaque region and the first surface of the adhesive region facing the user when the main body is extended over the user's eyes, the first surface of the adhesive region being axially offset from the inner surface of the opaque region.

16. The sleep mask apparatus recited in claim 15, wherein the main body includes an opening, the adhesive region circumnavigating the opening and the opaque region extending over the opening.

17. The sleep mask apparatus recited in claim 15, wherein the adhesive region completely circumnavigates the opaque region.

18. The sleep mask apparatus recited in claim 15, wherein the main body includes at least one opening, the adhesive region circumnavigating the at least one opening, and the opaque region comprising a cup element defining a substantially concave surface and an opposing substantially convex surface, the cup element extending over the at least one opening.

19. A sleep mask, comprising:
   an annular flexible member defining an opening, said annular flexible member comprising:
   an inner surface for contacting a wearer's face, said inner surface including at least one adhesive region, said adhesive region including adhesive for releasably securing the inner surface to a wearer's face; and
   an opposed outer surface to said inner surface;
   an opaque body configured to be positioned over a wearer's eyes having an inner and outer surface; and
   at least one intermediate member coupled to the outer surface of said annular flexible member and the inner surface of said opaque body so as to at least partially overlap said annular flexible member and said opaque body, the at least one intermediate member extending inwardly from the inner side of said opaque body to define a space between the wearer's face and said opaque body, the at least one intermediate member having an outer periphery offset from an outer periphery of the annular flexible member and positioned inwardly from the outer periphery of the annular flexible member;
   the annular flexible member, the opaque body, and the at least one intermediate member having a void extending from the opaque body to the inner surface of the support element, the void being placeable over the wearer's eyes such that at least a portion of the user's eyelids protrude into the void.

20. The sleep mask recited in claim 19, wherein the opening in the annular flexible member is a single opening.

21. The sleep mask recited in claim 19, wherein the opening in the annular flexible member includes a pair of openings.

22. The sleep mask apparatus recited in claim 1, wherein the support element includes an inner periphery and the spacer includes an inner periphery offset from the inner periphery of the support element and positioned inwardly from the inner periphery of the support element.

* * * * *